United States Patent
Nagaoka et al.

(10) Patent No.: US 7,498,317 B2
(45) Date of Patent: Mar. 3, 2009

(54) ANTIBACTERIAL AGENTS AND PROCESS FOR PRODUCING THE SAME

(75) Inventors: Masato Nagaoka, Tokyo (JP); Hideyuki Shibata, Tokyo (JP); Itsuko Takagi, Tokyo (JP); Shusuke Hashimoto, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 451 days.

(21) Appl. No.: 11/049,423

(22) Filed: Feb. 2, 2005

(65) Prior Publication Data

US 2005/0130934 A1    Jun. 16, 2005

Related U.S. Application Data

(63) Continuation of application No. 09/806,650, filed as application No. PCT/JP99/05448 on Oct. 4, 1999, now abandoned.

(30) Foreign Application Priority Data

Oct. 5, 1998    (JP) .................................. 10-282143

(51) Int. Cl.
  *A61K 31/731*  (2006.01)
  *A61K 31/737*  (2006.01)
(52) U.S. Cl. ............................. 514/54; 514/53; 514/62
(58) Field of Classification Search ........................ None
  See application file for complete search history.

(56) References Cited

U.S. PATENT DOCUMENTS

| | | | |
|---|---|---|---|
| 4,153,686 A | 5/1979 | Nagel | |
| 4,489,065 A | 12/1984 | Walton et al. | |
| 5,336,506 A | 8/1994 | Josephson et al. | |
| 5,476,669 A | 12/1995 | Borody | |
| 6,011,008 A | 1/2000 | Domb et al. | |

FOREIGN PATENT DOCUMENTS

| | | | |
|---|---|---|---|
| EP | 125759 | * | 3/1984 |
| EP | 0 392 487 A | | 10/1990 |
| EP | 0645143 A | | 3/1995 |
| JP | 54-46836 A | | 4/1979 |
| JP | 54-46840 A | | 4/1979 |
| JP | 4-500798 A | | 2/1992 |
| JP | 7-138166 A | | 5/1995 |
| JP | 8-333213 A | | 12/1996 |
| JP | 10-114660 A | | 5/1998 |
| JP | 10-155898 A | | 6/1998 |
| JP | 11-60590 A | | 3/1999 |
| WO | WO 89/05646 | | 6/1989 |
| WO | WO 95/34571 A | | 12/1995 |
| WO | WO 97/37680 A1 | | 10/1997 |
| WO | WO 98/37915 A | | 9/1998 |
| WO | WO 99/10360 | | 3/1999 |

* cited by examiner

*Primary Examiner*—Leigh C Maier
(74) *Attorney, Agent, or Firm*—Frishauf, Holtz, Goodman & Chick, P.C.

(57) ABSTRACT

An antibacterial agent showing a high affinity for *Helicobactor pyroli* and having an antibacterial effect specific to *H. Pyroli*. The agent has a chemical structure wherein an antibacterial substance is bonded to a sulfated polysaccharide or an oligosaccharide prepared by partial decomposition of the sulfated polysaccharide. Preferable embodiments are those having the chemical structure represented by Y—OCH(AH$_2$NHR)$_n$ or Y—BH$_2$NHR, wherein Y represents a sulfated polysaccharide or an oligosaccharide prepared by partial decomposition of the sulfated polysaccharide; A a carbon derived from aldehyde group occurring through the reduction of the reduced end sugar of Y and subsequent oxidation of the resulting product with an oxidant; B a carbon derived from the aldehyde group at the reduced end sugar of Y; R an antibacterial substance with a primary amino group or with an amino group introduced therein or represents an antibacterial substance derivative prepared by bonding an antibacterial substance through a spacer to the carbon A or the carbon B; and n=1 or 2.

6 Claims, 2 Drawing Sheets

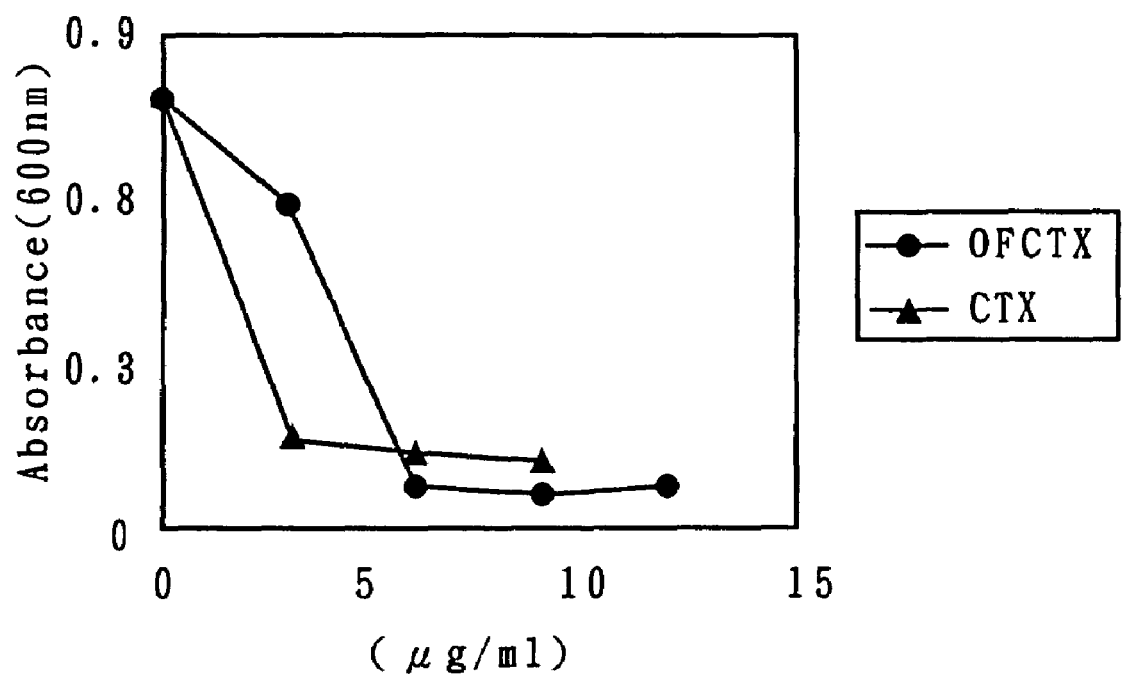
F I G. 2

ANTIBACTERIAL AGENTS AND PROCESS FOR PRODUCING THE SAME

This application is a Continuation Application of Ser. No. 09/806,650, filed Apr. 2, 2001, now abandoned which is the U.S. national phase application of International Application No. PCT/JP99/05448, filed Oct. 4, 1999, which is incorporated herein by reference in its entirety.

TECHNICAL FIELD

The present invention relates to an antibacterial agent. More specifically, the invention relates to sulfated polysaccharides and oligosaccharide derivatives prepared by partially decomposing sulfated polysaccharides, which are effective for the eradication of *Helicobactor pylori* as the etiological microorganism of gastric ulcer or gastric cancer and typically include fucoidan, and a method for preparing the same.

As the therapeutic agent of gastric ulcer, traditionally, use has generally been made of $H_2$ blockers and proton pump inhibitors for the purpose of the secretory suppression of gastric acid, and gastric mucosa protectors. Although these drugs exert significant therapeutic effects, it has been known that gastric ulcer repeatedly relapses in individuals infected with *Helicobactor pylori*.

Additionally, it has been known that individuals infected with *Helicobactor pylori* are at a high statistical frequency of the occurrence of gastric cancer. From the respect of the radical treatment of gastric ulcer or the prophylaxis of gastric cancer, it is remarked that a therapeutic treatment including the eradication of *Helicobactor pylori* is needed (M. Asaka, "*Helicobactor pylori* and Gastric Mucosa Diseases", Sentan Igaku Corp., Jul. 1, 1995; Digestive Disease Society of Japan edit., "Guidline Reference for *Helicobactor pylori* Therapy", *H. pylori* Therapy Committee).

Based on these remarks, the eradication/therapeutic treatment in combination with antibiotics and gastric acid secretion-suppressive agents has been conducted. However, problems occur, such as the incidence of diarrhea and the emergence of resistant bacteria, because of the relatively high doses of antibiotics, although the treatment has a high eradication effect.

Alternatively, the present inventors have found that oligosaccharide derivatives prepared from partially decomposed products of Nemacystus decipiens and green laver exert not only an action to promote the therapy of gastric ulcer but also exert an inhibitory action against the fixation of *Helicobactor pylori* and an antibacterial action against the microorganism (JP-A-11-60590). However, the antibacterial action of the derivative substances is not yet satisfactory although the derivative substances have a strong action to promote the therapy of ulcer.

In such situation, the inventors have made investigations. Consequently, the inventors have prepared saccharide derivatives by modifying sulfated polysaccharides into oligosaccharide with acid treatment and additionally subjecting the resulting oligosaccharide to periodate oxidation, reaction with corresponding amines (antibacterial substance) and reductive treatment. Then, the inventors have verified that sulfated polysaccharides and the resulting saccharide derivatives have high affinity for *Helicobactor pylori* to show an excellent antibacterial effect. Hence, the invention has been achieved.

It is an object of the invention to provide an antibacterial agent with high affinity for *Helicobactor pylori* to exert an antibacterial effect specific to *Helicobactor pylori*.

DISCLOSURE OF THE INVENTION

The antibacterial agent of the present invention is of a chemical structure containing a sulfated polysaccharide or an oligosaccharide prepared by partial decomposition of said sulfated polysaccharide and an antibacterial substance chemically bonded to said sulfated polysaccharide or said oligosaccharide.

Preferably, the antibacterial agent of the present invention has a chemical structure represented by either one of the following formulae:

wherein, Y represents a sulfated polysaccharide or an oligosaccharide prepared by partial decomposition of the sulfated polysaccharide; A represents a carbon derived from aldehyde group occurring through the reduction of the reduced end sugar of Y and subsequent oxidation of the resulting product with an oxidant; B represents a carbon derived from the aldehyde group at the reduced end sugar of Y; R represents an antibacterial substance with a primary amino group or with an amino group introduced therein or represents an antibacterial substance derivative prepared by bonding an antibacterial substance through a spacer to the carbon A or the carbon B; and n=1 or 2.

In a preferred embodiment of the present invention, the sulfated polysaccharide or oligosaccharide prepared by partial decomposition of said sulfated polysaccharide is selected from the group consisting of fucoidan, oligofucose prepared by partial decomposition of fucoidan, carrageenan and carrabiose prepared by partial decomposition of carrageenan.

The present invention also provides an antibacterial agent for use in the eradication of *Helicobactor pylori*, said agent comprising the aforementioned antibacterial agent as an effective component together with a pharmaceutically acceptable carrier or excipient in liquid or solid.

The present invention additionally provides a prophylactic and therapeutic agent of gastric ulcer, comprising the aforementioned antibacterial agent as an effective component together with a pharmaceutically acceptable carrier or excipient in liquid or solid.

According to another aspect of the present invention, there is provided a method for producing the antibacterial agent containing a sulfated polysaccharide or an oligosaccharide prepared by partial decomposition of the sulfated polysaccharide and an antibacterial substance chemically bonded to the sulfated polysaccharide or the oligosaccharide, said method comprising the steps of:

opening the ring of the aldehyde group of the sugar residue remaining at the reduced end of the sulfated polysaccharide or the oligosaccharide, directly or through oxidative decomposition, to recover an oligosaccaride fraction;

allowing the amine group of an antibacterial substance corresponding to the ring-opened aldehyde group to react with said oligosaccharide fraction to prepare a Schiff base; and reducing the resulting Schiff base.

In the antibacterial agent of the present invention, an antibacterial substance is bonded to a sulfated polysaccharide or an oligosaccharide prepared by partial decomposition the sulfated polysaccharide, such as fucoidan, carrageenan, rhamnan sulfate, chondroitin sulfate, heparin, dermatan sulfate and keratan sulfate. Therefore, the antibacterial agent has high affinity for *Helicobactor pylori* and exerts an antibacterial effect specific to *Helicobactor pylori*.

More specifically, the sulfated polysaccharide or oligosaccharide prepared by partial decomposition thereof has high affinity for *Helicobactor pylori*, so that the sulfated polysaccharide or oligosaccharide is adsorbed or bonded to *Helicobactor pylori* to inhibit the fixation of *Helicobactor pylori* on gastric wall. Using the specificity of the sulfated polysaccharide or oligosaccharide prepared by partial decomposition thereof to *Helicobactor pylori*, the present invention provides an antibacterial agent prepared by binding an antibacterial substance to a sulfated polysaccharide or oligosaccharide, namely a novel antibacterial agent capable of effectively allowing the antibacterial substance to exert the action against *Helicobactor pylori*.

It is contemplated that fucoidan or carrageenan, particularly, fucoidan might be preferable as the sulfated polysaccharide used in the present invention because of resultant high antibacterial effect.

Since the antibacterial agent according to the present invention has an antibacterial effect on pathological bacteria other than *Helicobactor pylori*, the antibacterial agent may also be applicable to these pathological bacteria.

In a preferred embodiment of the present invention, the antibacterial agent has a chemical structure comprising a sulfated polysaccharide or an oligosaccharide prepared by partial decomposition of the sulfated polysaccharide and an antibacterial substance chemically bonded to the reduced end of the sulfated polysaccharide or the oligosaccharide, said chemical structure being represented by either one of the following formulae:

Y—OCH(AH$_2$NHR)$_n$ or Y—BH$_2$NHR wherein, Y represents a sulfated polysaccharide or an oligosaccharide prepared by partial decomposition of the sulfated polysaccharide; A represents a carbon derived from aldehyde group occurring through the reduction of the reduced end sugar of Y and subsequent oxidation of the resulting product with an oxidant; B represents a carbon derived from the aldehyde group at the reduced end sugar of Y; R represents an antibacterial substance with a primary amino group or with an amino group introduced therein or represents an antibacterial substance derivative prepared by bonding an antibacterial substance through a spacer to the carbon A or the carbon B; and n=1 or 2.

More specifically, Y in the formula is a sulfated polysaccharide or an oligosaccharide prepared by the partial decomposition thereof, such as fucoidan, carrageenan, rhamnan sulfate, chondroitin sulfate, heparin, dermatan sulfate and keratan sulfate, wherein some of the hydroxyl groups may be modified into sulfated esters. As the sulfated polysaccharide, use can be made of oligosaccharide adjusted to a molecular weight of about 300 to 5,000, preferably, 300 to 1,000, through a combination of ultrafiltration membranes with different fractionation sizes. In such case, a high antibacterial effect can be recovered at a smaller quantity of antibiotics. Especially, preferable are fucoidan of a molecular weight of about 300 to 5,000, particularly 500 to 3,000 and carrageenan of a molecular weight of about 300 to 2,000, particularly 300 to 900.

R in the formula is an antibacterial substance with a primary amine or with an amino group introduced therein, such as cefem series, penicillin series, aminoglycoside series, macrolide series, pyridocarboxylate series, oxafem series, monobactam series, carbapenem series, tetracycline series, peptide series, chloramphenicol and sulfa agents, or derivatives thereof with spacers introduced therein.

More specifically, cefem antibacterial agents include cefotaxime, cephalotin, cephaloridine, cephalexin, cefradine, cefazolin, ceftezol, cephapirin, cephacetrile, cefoxitin, cefinetazole, cefroxime, cefotiam, cephamandole, cefsulodine, ceftizoxime, ceftazidime, cefotetan, cefinenoxime, ceftriaxone, cefoperazone, cefbuperazone and cefixime.

Penicillin antibacterial agents include ampicillin, benzyl-PC, phenethicillin, propicilin, methicillin, zxacillin, cloxacillin, amoxicillin, cyclacillin, carbenicillin, sulbenicillin and piperacillin.

Aminoglycoside antibacterial agents include kanamycin, bekanamycin, tobramysin, dibekacin, gentamicin, amikacin, habekacin, neomycin B and paromomycin.

Macrolide antibacterial agents include erythromycin, kitasamycin, acetylkitasamycin, oleandomycin, josamycin, acetylspiramycin and midecamycin.

Pyridocarboxylate antibacterial agents include nalidixic acid, oxolinic acid, norfloxacin, piromidic acid, ofloxacin and ciprofloxacin.

Oxafem antibacterial agents include latamoxef.

Monobactam antibacterial agents include sulfazecin and monobactam.

Carbapenem antibacterial agents include thienamycin.

Tetracycline antibacterial agents include tetracycline, chlortetracycline, oxytetracycline, demethl chlortetracycline, doxycycline, methacycline, and minocycline.

Peptide antibacterial agents, other than those included in any of the individual antibacterial agents described above, include gramicidin, penicillin, polymyxin, gramicidin S, viomycin and actinomycin.

These antibacterial agents have so high affinity for *Helicobactor pylori*, in particular, that each of the antibacterial agents is adsorbed or bonded specifically to *Helicobactor pylori*. Thus, each of the antibacterial agents is particularly effective as an antibacterial agent for use against *Helicobactor pylori*. Furthermore, the antibacterial agent specifically inhibits *Helicobactor pylori* so the agent can be used as a prophylactic and therapeutic agent of gastric ulcer.

In order to prepare derivatives of a sulfated polysaccharide or of an oligosaccharide prepared by partial decomposition of the sulfated polysaccharide, use may be made, for example, the process for preparing oligofucose derivative, which process comprises the steps 1 to 8 as described hereunder.

Step 1: Extracting polysaccharides from sea algae (Phaeophyceae such as Nemacystus, Kurome and Fucus) containing fucoidan by known extraction processes (Cf. K. Matsuda., Biochemistry Experimental Methods, No. 20, "Separation and Purification of Polysaccharides", Gakkai Shuppan Center).

Step 2: Dissolving the resulting fucoidan in a hydrochloric acid solution or trifluoroacetic acid solution of about 0.05 M to 0.1 M, heating the resulting solution at 100° C. for 10 to 20 minutes to modify the fucoidan into oligosaccharide, and neutralizing the solution with sodium hydroxide. The oligosaccharide modification may satisfactorily be carried out by using fucoidanase (fucoidan decomposition enzyme). The reaction conditions then may appropriately be determined. The NaBH$_4$ is added to the oligosaccharide solution thus recovered, for reduction process at ambient temperature or 4° C. for 16 hours (Cf. JP-A-6-247861 and JP-A-7-138166).

Step 3: Desalting the solution of the oligosaccharide in the form of alditol as recovered by the procedures at the step 2, by electrodialysis (Microacylizer; manufactured by Asahi Chemical Industry, Co., Ltd.).

Step 4: Adding sodium metaperiodate to the solution at the step 3 for reaction at the temperature of ice for about one hour (the reaction time may satisfactorily be longer, depending on the structure of the sugar chain, for example the structure of an oligosaccharide with 1→3 bond). Ethylene glycol at a volume excessive to periodic acid is added to the reaction solution, for reaction for another hour. The resulting solution is desalted in the same manner as in the step 3. By the procedures, oligosaccharide with an aldehyde group at the reduced end thereof can be recovered.

Step 5: Acetic acid is added to the sample prepared at the step 4 to a concentration of 0.5 M, for reaction at ambient temperature for 20 hours (under conditions for no promotion of the oxidation of the sugar chains at the side of the non-reduced end, the procedure may be skipped). Using an ultrafiltration membrane or dialysis membrane for the intended fractionation molecular weight, the reaction solution is desalted while ethylene glycol and the decomposition products thereof are removed, to recover oligosaccharide. Additionally, the oligosaccharide fraction may be prepared into a desired molecular size, using active charcoal chromatography and gel filtration, other than the purification by these processes.

Step 6: The oligosaccharide fraction is dissolved in water, followed by addition of an antibacterial agent to be introduced therein, for reaction at ambient temperature for one hour, to prepare a Schiff base.

Step 7: Borane dimethylamine is added to the solution recovered at the step 6, for reaction at ambient temperature for 20 hours to reduce the Schiff base. As such reducing agent, any reducing agents suitable for the purpose of the invention can appropriately be used (for example, borane trimethylamine, $NaCNBH_3$, $NaBH_4$, etc.).

Step 8: After completion of the reaction, excess reagents are removed through ultrafiltration or dialysis. After removal of the excess reagents, the resulting reduced solution is dried by freeze-drying or further purified by ion exchange chromatography. It was verified that the oligosaccharide derivative thus recovered had high antibacterial effect against *Helicobactor pylori* as the etiological bacterium of gastric ulcer.

Polysaccharide derivatives prepared from fucoidan per se without the steps 2 and 3 can exert the same effect. The dose of the antibacterial agent of the present invention can appropriately be selected in the same manner as for general pharmaceutical drugs, preferably according to the prescription of doctor. For example, a derivative prepared from oligofucose of a molecular weight of 500 to 3,000 is administered at a dose of 100 mg/day to 500 mg/day per adult, particularly at 200 mg/day to 300 mg/day per adult. In such case, high antibacterial effect can be realized, together with the suppression of the side effects. The larger molecular weight of fucoidan necessitates the higher dose for a certain level of the antibacterial effect. Therefore, in case where fucoidan of another molecular weight value is used, the content of fucoidan may be appropriately adjusted in accordance with the molecular weight thereof.

The form of the antibacterial agent according to the present invention can be selected appropriately. Typically, the antibacterial agent is blended with a pharmaceutically acceptable carrier in liquid or solid, to which solvents, dispersants, emulsifiers, buffers, stabilizers, excipients, binders, disintegrators and/or lubricants are added if necessary, to formulate the antibacterial agent into tablets, granules, powders or capsules for use.

As described above, the present invention advantageously provides an antibacterial agent with high affinity for *Helicobactor pylori* and an antibacterial effect specific to *Helicobactor pylori*.

BRIEF DESCRIPTION OF DRAWINGS

FIG. 2 shows a graph depicting the inhibitory effects of OF-CTX and CTX on the growth of *Helicobactor pylori*; the abscissa represents turbidity (600 nm) and the ordinate represents the amounts added (μg/mL).

BEST MODE FOR CARRYING OUT THE INVENTION

EXAMPLE 1

Figure 1:
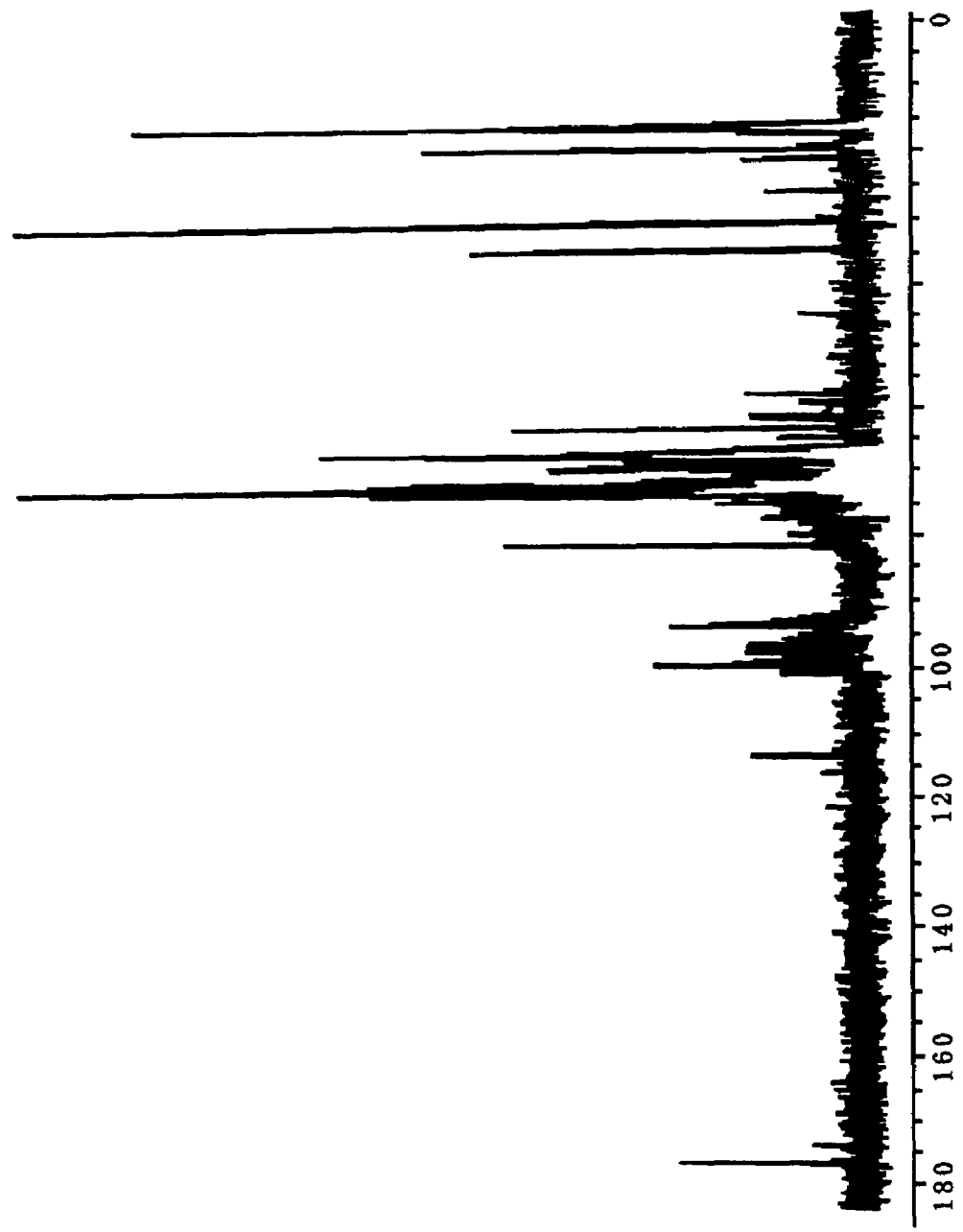
FIG. 1 shows a $^{13}C$-NMR chart of OF-CTX; the abscissa represents relative intensity of measured signal, while the ordinate represents frequency (Hz)

Production of Oligofucose Derivative (1.1) Fucoidan Extraction and Oligofucose Production

*Cladosiphon okamuranus Tolida* was desalted in deionized water. After that, the resulting alga was suspended in deionized water at a ratio of 1 kg of the alga per one liter of deionized water. With hydrochloric acid, the suspension was adjusted to pH 2. After heating the resulting solution at 100° C. for 10 minutes for extraction and filtering the alga through gauze, the resulting filtrate was further centrifuged to remove insoluble matters (9,000 rpm, 60 minutes).

After the supernatant was neutralized with NaOH, sodium metaperiodate was added to a final concentration of 0.2 M, to decompose contaminated components of alginic acid and uronic acid. After 20-hour reaction in darkness, the reaction was terminated with ethylene glycol. To the resulting solution was added sodium borohydride to a concentration of 0.2 M, for reaction at ambient temperature for 16 hours. The resulting solution was concentrated via ultrafiltration (fractionated molecular weight of 5,000), for dialysis. With hydrochloric acid, the dialyzed solution was adjusted to pH 2. Then, the solution was treated under heating at 10° C. for 10 minutes. After the treated solution was dialyzed and freeze-dried, fucoidan was recovered (4 g/1 kg of wet alga).

(1.2) Preparation and Periodate Oxidation of Oligofucose

Fucoidan was dissolved in distilled water to a concentration of 200 mg/mL, to which was added hydrochloric acid (or trifluoroacetic acid may be satisfactory) to a final concentration of 0.075 M to 0.1 M. After heating at 100° C. for 10 minutes, the resulting solution was cooled to ambient temperature. The solution was neutralized with NaOH, and then, $NaBH_4$ was added at a ratio of 200 mg per 1 g of fucoidan. The mixture reacted together at 4° C. for 20 hours.

The reaction solution was adjusted to pH6 with acetic acid, which was then desalted with an electrodialyzer (Asahi Chemical Industry, Co., Ltd.; Microacylizer; AC220 membrane was used). After desalting, $NalO_4$ was added to the sample solution to a final concentration of 0.2 M, for reaction at the temperature of ice for one hour. Ethylene glycol of 2 equivalents corresponding to that of periodic acid was added to the reaction solution, for further reaction at the temperature of ice for one hour. The reaction solution was filtered through an ultrafiltration membrane of a fractionation molecular weight of 1,000 (manufactured by Millipore Co.), for concentration. The inner solution was freeze-dried, to recover an aldehyde derivative of oligofucose (yield of about 25%).

(1.3) Coupling Reaction with Antibacterial Substance and Reduction

The aldehyde derivative (5 g) of the oligosaccharide as produced in (1.2) was dissolved in water (100 mL), followed by addition of cefotaxime (CTX) of 1 g. Adding 1 mL of 0.5 M $NaHCO_3$ solution, reaction progressed at ambient temperature for one hour. After the reaction, 1 g of borane dimethylamine complex was added, for reaction at ambient temperature for 20 hours. The reaction solution was dialyzed throughout the day against a dialysis membrane of a fractionation molecular weight of 1,000. The resulting solution was freeze-dried, to recover the objective sample OF-CTX (yield of 1.14 g). FIG. 1 shows $^{13}C$-NMR chart of the resulting OF-CTX. The structure of the OF-CTX is specifically shown by the following chemical formula (1).

Chemical formula (1)

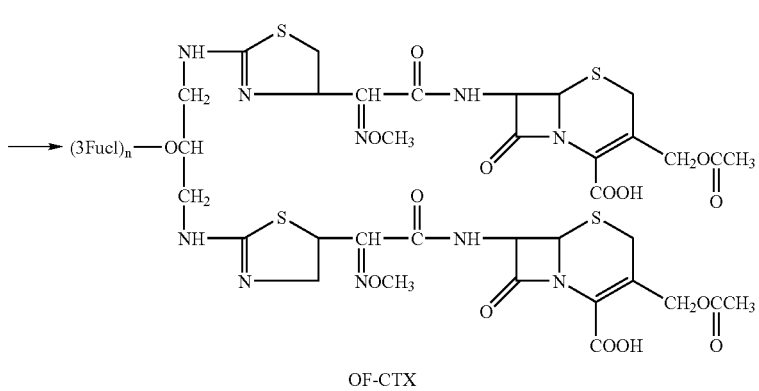

OF-CTX

In the same manner as in the case of (1.3), reaction progressed except that ampicillin was used instead of cefotaxime, to recover oligofucose ampicillin derivative OF-AM. The structure of the resulting OF-AM is specifically shown by the chemical formula (2) given below.

Oligofucose (2 g) was dissolved in 80 mL of aqueous 40% ethanol (0.05 M, $NaCO_3$). 350 mg of 12-aminolauric acid (C12) was added to the resulting solution, for reaction at 45° C. for one hour. 300 mg of borane dimethylamine was added, for reaction at 45° C. for 16 hours.

Chemical formula (2)

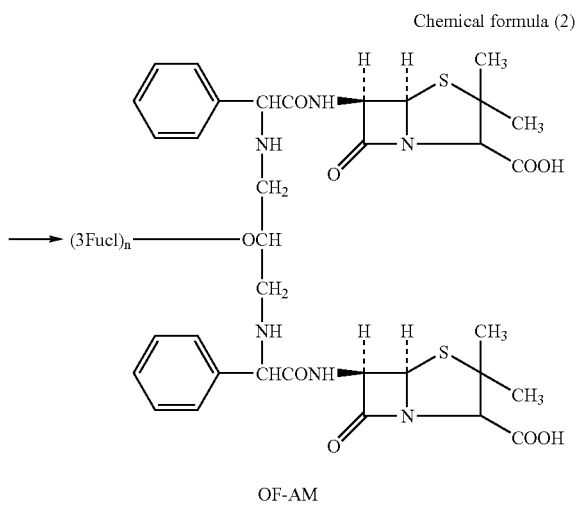

OF-AM

After the reaction, the solution was dialyzed against a dialysis tube of a fractionation molecular weight of 1,000 cut. The freeze-dried dialysis product (875 mg) was dissolved in 10 mL of water, followed by addition of 500 mg of EDC. After reaction at ambient temperature for 2 hours, 350 mg of cefotaxime Na was added, for reaction for 4 hours. Then, the solution was dialyzed against a dialysis membrane of a fractionation molecular weight of 1,000 for 2 days. The resulting solution was freeze-dried to recover a derivative OF-C12-CTX at a yield of 384 mg. The structure of the resulting OF-C12-CTX is specifically shown by the chemical formula (3) given below.

4.5 g of aminolauric acid was suspended in 200 mL of aqueous 30% ethanol, followed by appropriate addition of NaOH for dissolution. 14.5 g of oligofucose was added to the resulting solution, for reaction at 40° C. for one hour. After addition of 3 g of borane dimethylamine, reaction progressed at 40° C. for 20 hours. The resulting reaction solution was adjusted to pH 5 with hydrochloric acid, for centrifugation at 9,000 rpm for 15 minutes. The resulting supernatant was then dialyzed against a dialysis membrane of a fractionation molecular weight of 1,000 cut. After the dialyzed product was filtered and freeze-dried, an aminolaurate derivative of oligofucose was recovered (yield of 2.67 g).

The resulting derivative was suspended in 40 mL of water, followed by addition of methanol until the derivative was dissolved therein. The resulting solution was adjusted to pH 5 with hydrochloric acid, followed by addition of 3.5 g of water-soluble carbodiimide and 1.5 g of N-hydroxysuccinimide, for reaction at ambient temperature for 20 hours. The reaction solution was dialyzed and freeze-dried. The resulting dry product of 1.2 g was dissolved in water (20 mL).

Chemical formula (3)

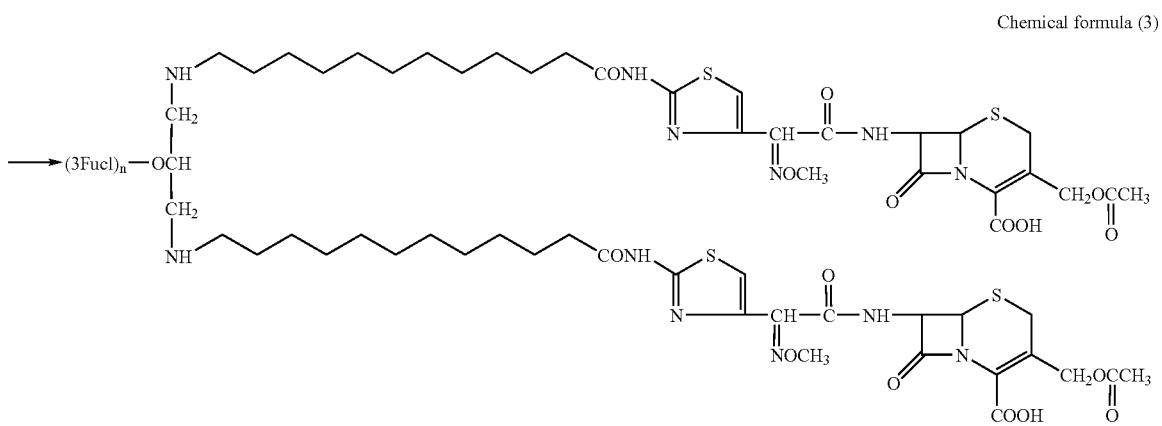

Sodium ampicillin (0.5 g) was added to the solution, followed by addition of 1 mL of 1 M NaHCO3. After reaction at ambient temperature for 20 hours, the reaction solution was dialyzed against a dialysis membrane of 1,000 cut. After the dialyzed inner solution was filtered and freeze-dried, an ampicillin derivative OF-C12-AM with a spacer introduced in the oligofucose therein was recovered (yield of 230.6 mg). The structure of OF-C12-AM thus recovered is specifically shown by the following chemical formula (4).

cefotaxime, alternatively, and the resulting mixture was dissolved in 20 mL of deionized water. These solutions were prepared as described above.

After reaction at 35° C. for one hour, 1 g of borane dimethylamine was added to the individual reaction mixtures, for reaction at 25° C. for 20 hours. To each of the reaction solutions was added 1 mL of 1 M acetate buffer, pH 4.6, which was then subjected to Microprep HIGHQ (15 ml) preliminarily equilibrated, for elution with 80 mL of 50 mM acetate Chemical formula (4)

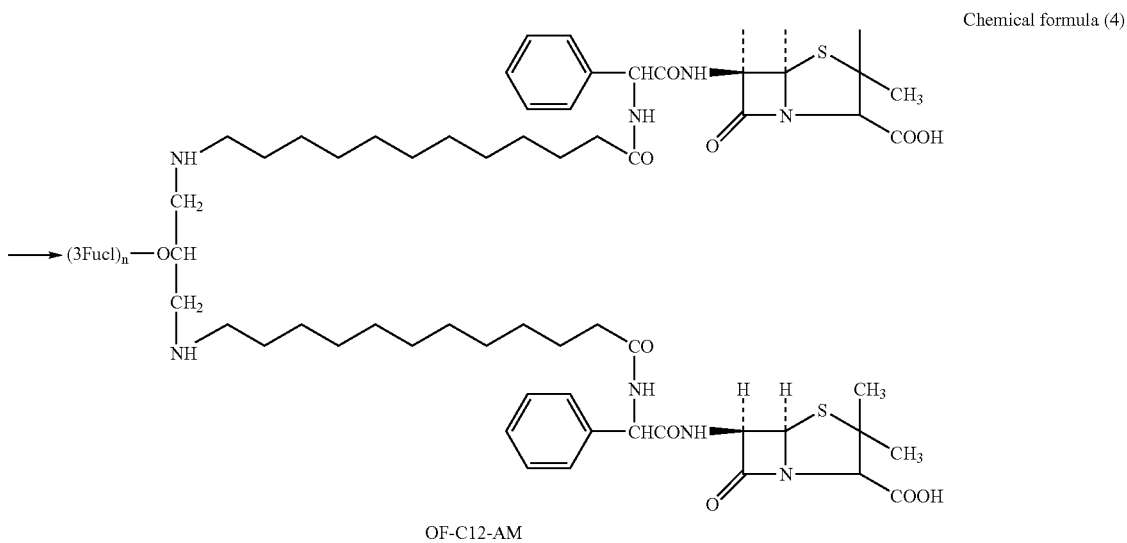

OF-C12-AM

EXAMPLE 2

Preparation of Carrabiose Derivative

Kappa carrageenan (10 g) was impregnated with water in 100 mL of 0.3N sulfuric acid. After permeation at 40° C. for 20 hours, heating was effected at 100° C. for 10 minutes. The resulting mixture was left to stand to ambient temperature, and was then neutralized. After removal of insoluble matters by centrifugation (20,000 rpm for 30 minutes), the resulting solution was desalted with Microacylizer and was then freeze-dried, to recover 9.74 g of carrabiose.

To 1 g of carrabiose thus recovered was added 1 g of ampicillin, and the resulting mixture was dissolved in 20 mL of deionized water. To 1 g of carrabiose was added 1 g of buffer. In such manner, unreactive antibiotics and borane are eluted. Continuously, 80 mL of the same buffer further containing 1 M NaCl was used for elution.

Collecting the fractions and desalting the fractions with electrodialysis, dialysis with a dialysis membrane of a fractionation molecular weight of 500 cut was promoted. Recovering and freeze-drying the dialyzed products, carrabiose ampicillin derivative (CarrabioAM) and carrabiose cefotaxime derivative (CarrabioCTX) were recovered at 587 mg and 437 mg, respectively.

The structures of the resulting carrabiose ampicillin derivative CarrabioAM and carrabiose cefotaxime derivative CarrabioCTX are specifically shown by the following chemical formulas (5) and (6), respectively.

Chemical formula (5)

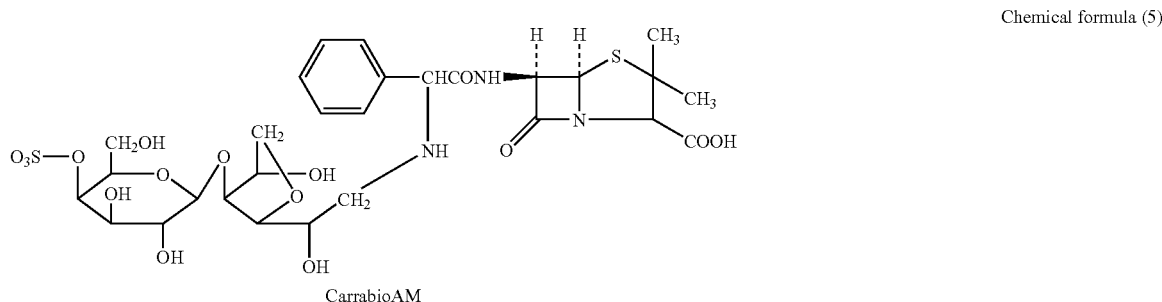

CarrabioAM

-continued

Chemical formula (6)

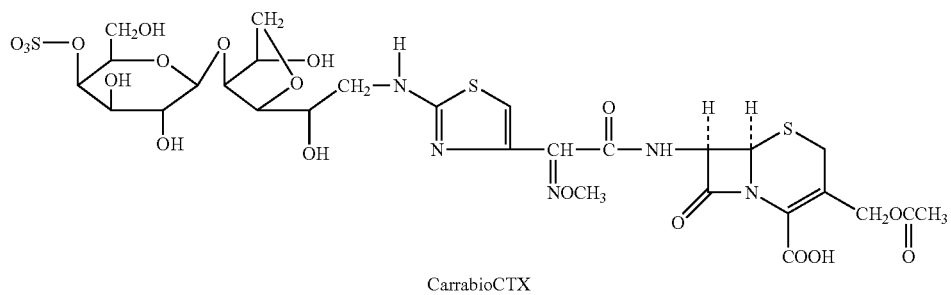

CarrabioCTX

EXAMPLE 3

Demonstration 1, Antibacterial Action to Helicobactor pylori

The activity inhibiting the growth of *Helicobactor pylori* was assayed by the following process. To 1 mL of the Brucella culture medium was added 100 µL of a clinical isolate *Helicobactor pylori* strain ($1.5 \times 10^8$ CFU/mL ), followed by addition of 0, 3, 6, 9 and 12 µL of 1 mg/mL OF-CTX or cefotaxime sodium CTX. After culturing at 37° C. for 3 days, the turbidity was assayed (at A600 nm), to count the growth ratio. The results are shown in FIG. 2.

As shown in the figure, OF-CTX at a concentration of 6 µg/mL almost thoroughly inhibited the growth of *Helicobactor pylori*. The activity was slightly lower than the activity of cefotaxime, but the cefotaxime content in the OF-CTX molecule was about 1/10 fold in molar ratio. Thus, it is indicated that the OF-CTX activity is higher than the activity of CTX alone.

EXAMPLE 4

Demonstration 2, Antibacterial Action to Helicobactor pylori

*Helicobactor pylori* is suspended in 25 mL of the Brucella culture medium. Then, each 500 µL portion is divided, to which is added 30 µL of the culture medium alone or 30 µL of the culture medium together with 1 mg/mL OF-CTX, for treatment at 0° C. for 0 to 25 minutes. After centrifugation at 14,000 rpm for 7 minutes, the precipitate is again suspended in 1 mL of the culture medium. The resulting suspension is divided in 100-µL portions. To the suspension is added 1 mL of the culture medium, for culturing at 37° C. for 3 days, to assay the turbidity at 600 nm. Consequently, the turbidity of the group preliminarily treated with OF-CTX is 0.153, while the turbidity of the control group is 0.494, which indicates that OF-CTX exerts a growth inhibitory effect at about 70%.

As described above, in accordance with the present invention, the derivatives of fucoidan and oligofucose have antibacterial actions against *Helicobactor pylori*. As shown in Example 4, these derivatives retain the effect after rinsing. Thus, it is indicated that these derivatives adhere to *Helicobactor pylori* and thus exert the effect. Hence, it is shown that these derivatives can be used as drugs advantageous for the therapeutic treatment of gastric ulcer and gastric cancer and as antibacterial agents with direction (specificity) to *Helicobactor pylori*.

EXAMPLE 5

Demonstration 3, Antibacterial Action to Helicobactor pylori

The culture of *Helicobactor pylori* was suspended in a Brucella culture medium containing 5% FCS to $1.5 \times 10^8$ CFU/mL. Each 200-µL portion was then inoculated in a 96-well microplate. Subsequently, each 2-µL portion of the carrabiose ampicillin derivative CarrabioAM or carrabiose cefotaxime derivative CarrabioCTX recovered in Example 2 (each at 1 mg/mL) was inoculated thereon. After agitation, the bacterium was cultured under slightly aerobic conditions at 37° C. for 3 days, to assay the turbidity at 600 nm. Consequently, the absorbance levels of the carrabiose ampicillin derivative CarrabioAM and the carrabiose cefotaxime derivative CarrabioCTX were 0.003 and 0.000, respectively, while the absorbance of the control group was 0.835. Hence, it is indicated that these antibacterial agents totally suppressed the growth of *Helicobactor pylori*.

We claim:

1. An antibacterial agent having a chemical structure comprising a sulfated polysaccharide or an oligosaccharide prepared by partial decomposition of said sulfated polysaccharide and an antibacterial substance chemically bonded to the reduced end of said sulfated polysaccharide or of said oligosaccharide, wherein said sulfated polysaccharide or said oligosaccharide prepared by partial decomposition of said sulfated polysaccharide is selected from the group consisting of fucoidan, oligofucose prepared by partial decomposition of fucoidan, carrageenan and carrabiose prepared by partial decomposition of carrageenan, and wherein said chemical structure is represented by either one of the following formulae:

wherein Y represents said sulfated polysaccharide or said oligosaccharide prepared by partial decomposition of the sulfated polysaccharide; A represents a carbon derived from an aldehyde group occurring through the reduction of the reduced end sugar of Y and subsequent oxidation of the resulting product with an oxidant; B represents a carbon derived from the aldehyde group at the reduced end sugar of Y; R represents an antibacterial substance with a primary amino group or with an amino group introduced therein or represents an antibacterial substance derivative prepared by bonding an antibacterial substance through a spacer to the carbon A or the carbon B; and n=1 or 2.

2. An antibacterial agent for use Against *Helicobactor pylori*, comprising an antibacterial agent according to claim 1 as an effective component together with a pharmaceutically acceptable carrier or excipient.

3. A prophylactic and therapeutic agent for gastric ulcer, comprising an antibacterial agent according to claim 1 as an effective component together with a pharmaceutically acceptable carrier or excipient.

4. An antibacterial agent according to claim 1, wherein said chemical structure is $Y-OCH(AH_2NHR)_n$.

5. An antibacterial agent according to claim 1, wherein said chemical structure is $Y-BH_2NHR$.

6. A method for producing an antibacterial agent as set forth in claim 1 comprising the steps of:

opening the ring of the aldehyde group of the sugar residue remaining at the reduced end of the sulfated polysaccharide or of the oligosaccharide prepared by partial decomposition of the sulfated polysaccharide, directly or through oxidative decomposition, to recover an oligosaccharide fraction; allowing the amine group of an antibacterial substance corresponding to the ring-opened aldehyde group to react with said oligosaccharide fraction to prepare a Schiff base; and reducing the resulting Schiff base.

* * * * *